United States Patent [19]
Prince

[11] 3,935,452
[45] Jan. 27, 1976

[54] QUADRUPOLE MOBILITY SPECTROMETER

[75] Inventor: Robert H. Prince, Unionville, Canada

[73] Assignee: Barringer Research Limited, Rexdale, Canada

[22] Filed: Nov. 14, 1973

[21] Appl. No.: 415,747

[52] U.S. Cl. ............................. 250/283; 250/292
[51] Int. Cl. ..................... H01j 39/34; B01d 59/44
[58] Field of Search ............ 250/292, 282, 283, 284

[56] References Cited
UNITED STATES PATENTS

| | | | |
|---|---|---|---|
| 3,641,340 | 2/1972 | VanDerGrinten | 250/292 |
| 3,784,814 | 1/1974 | Sakai | 250/292 |

*Primary Examiner*—James W. Lawrence
*Assistant Examiner*—C. E. Church
*Attorney, Agent, or Firm*—Rogers, Bereskin & Parr

[57] ABSTRACT

The present invention relates to an atmospheric pressure quadrupole mobility spectrometer for detecting and identifying trace amounts of various molecular species present in a gas. The invention includes an outer housing comprising forward and rear sections which define forward and rear chambers. The gas under analysis is caused to flow into the inlet part of the forward section where ionizers mounted around the circumference of the forward chamber convert a portion of the molecular species present in the gas into stable molecular ions suitable for analysis. Towards the center portion of the forward chamber a carrier gas is mixed with gas and ions so formed. Four parallel, cylindrical electrodes symmetrically positioned about the longitudinal axis of the rear chamber are connected in opposing pairs to a bipolar power supply which supplies a predetermined repetitive voltage waveform to the electrodes thereby creating a generally hyperbolic electric field between the electrodes. The gas under analysis containing the molecular ions and the carrier gas flow between the electrodes where the molecular ions interact with the electric field. The electric field is such that only molecular ions of the predetermined "mobility" will undergo stable trajectories through the electric field and emerge to strike a detector located adjacent to the outlet side of the rear chamber. All other molecular ions undergo unstable trajectories as they pass through the electric field and eventually strike one or other of the electrodes and are discharged before reaching the detector.

6 Claims, 3 Drawing Figures

QUADRUPOLE MOBILITY SPECTROMETER

The present invention relates to an atmospheric pressure quadrupole mobility spectrometer for use in detecting and identifying trace amounts of elements or compounds present in gases and more particularly it provides a non-chemical method of analyzing atmospheric gases in a quantitative manner. As such the present invention may be employed to analyze the atmosphere for pollutants and contaminants, both natural and man-made, as a tool in geochemical surveys and to detect contraband. In addition, certain medical and psychological disorders have odours associated with them that have been identified as due to specific compounds manufactured by the body. For example, the characteristic odour associated with the breath of a diabetic has been identified as due to the presence of ketone bodies including acetone. The present invention can be used as a diagnostic tool providing a sensitive method for the direct detection of such odours.

Presently available methods of non-chemical quantitative atmospheric analysis ordinarily require the use of instruments which employ high vacuums such as a vacuum mass spectrometer. For example, gas chromatography can be employed to achieve the temporal separation of gases in a sample based on differences in the structure of the various molecular species present in the gas sample. However, the results require careful interpretation since the mass of each species is not directly measured but rather a transport property related to mass, called the diffusion constant, is measured. A more directly interpretable measurement can be made by performing a routine vacuum mass spectrometer analysis. The vacuum mass spectrometer may be one of a variety of types available although magnetic deflection, time of flight, monopole or quadrupole instruments are usually selected. However, the high vacuum pumping required by such instruments is accompanied by the disadvantages of high cost, complexity and weight.

An alternate transport property useful for mass identification of a molecule is the "ion mobility" of the molecule as it passes through a gas. Although "ion mobility" is functionally related to the size of a molecular ion rather than its mass the uniqueness of mass identification from mobility data is much better than predicted by early theoretical work. More recent theoretical and experimental analysis indicates that a good correlation exists between "ion mobility" and mass for relatively heavy molecular ions, particularly where a specific class of molecules is concerned.

A relatively new technique known as plasma chromatography has been shown to be sensitive to gas molecular concentrations of less than 0.1 parts per billion. This technique creates primary ions in a reactant gas containing a sample of the gas and trace organic molecular species under analysis by means of an ionizing $\beta$-ray radiation source. The primary ions initiate a sequence of ion molecular reactions rapidly yielding several molecular ions which react with the trace impurities in the reactant gas to form stable molecular ions suitable for analysis. This technique utilizes a uniform axial electric field provided by a plurality of precision stacked rings which form a drift tube. The stable molecular ion forms of the various molecular species are directed into one end of the drift tube where under the influence of an axial electric field they drift through a carrier gas present in the drift tube. At the other end of the drift tube the molecular ions are collected at a detector. The transit time for each species of molecular ion is a function of its interaction with the carrier gas and the electric field in drift tube. The transit time of the various molecular ions related to the mobility by the following mathematical expression:

$$K = v/E$$
$$= \chi/\tau.E$$

where
$K=$ molecular ion mobility in cm$^2$/volt -second
$v=$ drift velocity in cm/second
$E=$ axial electric field intensity in VOLTS/CM
$\chi=$ transit distance in cm
$\tau=$ transit time in seconds The molecular ions produced in the reaction zone must be introduced to the drift tube by means of an electrical shutter. The electrical shutter is held at a high potential during the drift interval in order to repel the molecular ions which have entered the drift tube. Either positive or negative ions, but not both, may be admitted into the drift tube by employing the appropriate voltage polarity on the shutter. Since the number of molecular ions admitted into the drift tube during the interval that the shutter is open is quite small and becomes dispersed with respect to arrival time at the downstream detector and continuous sampling is hindered by the need for an electrical shutter, discreet analysis is usually required. Consequently, many injection-drift cycles are required during a scan necessitating a relatively long scan time and data storage. Data storage is expensive and furthermore results in an inherent limitation in resolution.

The present invention provides an alternative method for obtaining molecular species separation based on differences in molecular ion mobilities. Employing the quadrupole field principle, a transverse electric field is applied to the molecular ions in a gas sample and the apparatus is electrically tuned to obtain a stable oscillatory trajectory for a particular unique value of molecular ion mobility. Consequently molecular ions having a mobility other than the selected mobility will not pass through the apparatus to the detector.

Accordingly, in one of its aspects the present invention provides a spectrometer of reduced mechanical and electrical complexity for quantitative, non-chemical analysis of trace compounds in gases.

According to another aspect of the present invention a spectrometer is provided for analyzing trace compounds in gases in which the mass resolution of the apparatus is not limited by data storage, is continuously variable and can be held constant during a mobility scan.

These and other aspects of the present invention will be more readily understood by reference to the accompanying description and drawings, wherein.

In order to make the detailed description of the present invention more readily understandable a general explanation of the basic theory of the present invention will first be given.

Functionally a mobility spectrometer is an apparatus adapted to detect and identify specific molecular species in a gas at atmospheric pressure without the need for high vacuums. To accomplish this result the mobility spectrometer makes use of the relationship which exists between the mass and the mobility of a molecular ion form of a molecular species. In a simple form a mobility spectrometer includes four parallel, cylindrical electrodes symmetrically placed about a longitudinal axis and electrically connected in opposite pairs to a bipolar power supply. The power supply provides an output voltage waveform adapted to create a predetermined transverse hyperbolic electric field pattern between the electrodes. The trace amounts of the molecular species in the gas under analysis are ionized by β-ray radiation to form stable molecular ions. The molecular ions are next introduced into the region between the electrodes with an initial axial speed which carries some of them through the inner electrode region to a detector. The detector may be unipolar or bipolar depending on whether positive or negative molecular ions or both positive and negative molecular ions are being analyzed.

The electric field causes the molecular ions to oscillate in a transverse direction with respect to the electrodes. The molecular ions can follow an oscillatory trajectory which may be a stable one in which the molecular ions execute oscillations with a restricted amplitude. On the other hand the molecular ion trajectories may be unstable in which case the molecular ions undergo oscillations of ever increasing amplitude until they collide with one or another of the field electrodes and discharge. For a given electric field only the specific mobility of the molecular ion determines whether the path is stable or unstable. In general the point of injection and the direction and magnitude of the initial injection speed have no bearing on the issue of whether or not a particular molecular ion species will follow a stable or unstable trajectory in the inner electrode space.

The field electrodes must be long enough to permit the molecular ions to execute a sufficiently large number of oscillations during the transit through the electric field. This is necessary in order to ensure that unstable molecular ions are discharged and hence do not reach the detector. By altering the power supply waveform in a predetermined manner the mobility spectrometer can in effect be tuned to eliminate all molecular species but the one having the desired "mobility". Thus, a positive means of identifying molecular species in a gas is provided.

Figure 1:
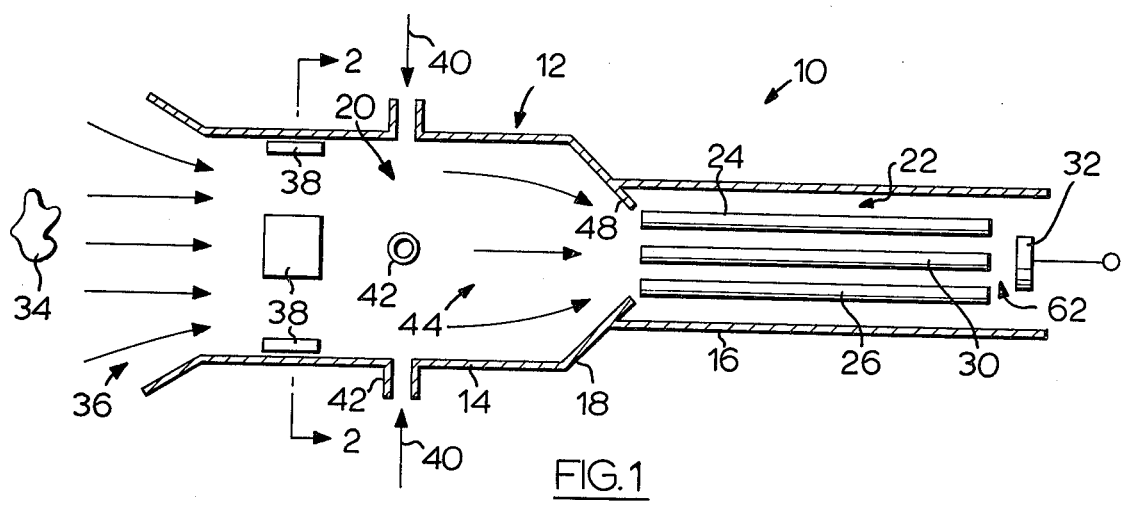
FIG. 1 is a diagrammatic sectional side view of an atmospheric pressure quadrupole mobility spectrometer according to the present invention.

Referring to FIG. 1, a mobility spectrometer 10 includes a hollow, thin walled, generally cylindrical outer housing 12 having an open ended forward section 14 and a relatively smaller diameter open-ended rear section 16 joined by a reducing section 18. Forward section 14 and rear section 16 define forward and rear chambers 20 and 22 respectively. A portion of housing 12 adjacent to the front end of section 14 is moderately flared to allow the smooth entry of gases into chamber 20 as will be described. Reducing section 18 is contoured to avoid causing turbulence in the gas flow as the gas under analysis flows into the central axial region of chamber 20.

Rear section 16 encloses four conductive electrodes 24, 26, 28, 30 (see also FIG. 2) positioned symmetrically around the longitudinal axis of section 16 in a quadrupole configuration. In the preferred embodiment of the present invention the electrodes are cylindrical in shape, have a predetermined length and diameter and are positioned at a predetermined distance $r_o$ (see FIGS. 2 & 3) from the longitudinal axis of section 16. In addition, a detector 32 is located in cavity 22 adjacent to the exit end of rear section 16.

A gas 34 containing trace amounts of the various molecular species under analysis is caused to flow continuously into the entry end of section 14, as indicated by arrows 36, with an initial axial speed. Gas 34 may be atmospheric air or any appropriate gas, such as flue gas or natural gas containing trace amounts of various molecular species to be analyzed. If the mobility spectrometer is being employed to analyze atmospheric gases and is mounted on a moving vehicle, such as an aircraft or automobile, the initial axial speed of gas 34 may be provided by a passive flow force such as laminar flow duct (not shown) which makes use of the ram effect provided by movement through the atmosphere. Alternatively, an active flow force employing a closed cycle aspirator or the like (not shown) may be employed. The latter means for providing a positive axial gas flow, although not absolutely essential, is preferable since it allows the axial speed of gas 34 to be made independent of the vehicle's motion. Furthermore, the use of an active flow force becomes a necessary requirement when the mobility spectrometer is employed in stationary ground applications. However, it is emphasized that the axial speed of gas 34 need not be uniform with regard to either the molecular species or time since it is the transverse motion rather than the axial motion of the molecular ions formed from the trace molecular species in gas 34 that is of importance. The basic limitation on the axial speed of gas 34 is established by the laminar flow requirements for the gas as it flows into outer housing 12.

Upon entering chamber 20 gas 34 is ionized by β-rays from ionizers 38. In the preferred embodiment of the present invention four ionizers are located symmetrically around the inner circumference of forward section 14 adjacent to its entry end. In their simplest form, ionizers 38 may be a radioactive form of nickel or tritium which emit β-rays of a predetermined energy. The ionizing effect of the radiation results in a portion of the trace compound contained in gas 34 being converted into stable molecular ions suitable for subsequent analysis.

A carrier gas represented by arrow 40 in FIG. 1, preferably dry air or an inert gas, is directed from a storage container (not shown) into chamber 20 via one or more inlet ports 42 in communication with chamber 20. The carrier gas mixes with the molecular ion species now present in gas 34 and the mixture flows into chamber 22 as indicated by arrows 44. Other methods for introducing the carrier gas will be apparent to those skilled in the art. For example, the carrier gas could be introduced into chamber 20 ahead of ionizers 38. In this case the carrier gas may include a high ionizable reactant material which subsequent to ionization readily gives up most of its charge to the trace molecular species in gas 34 thereby aiding in the formation of stable molecular ions.

The use of a carrier gas either with or without an added reactant material is not absolutely essential to the operation of the mobility spectrometer. However, the presence of a carrier gas is desirable for a number of reasons. First, the carrier gas provides a controlled, known medium having relatively well defined properties through which the molecular ions move while in chamber 22. A second reason for employing a carrier gas is related to the transfer of charge from the molecular ions to free water vapour present in gas 34. The presence of a dry carrier gas tends to reduce the degree of charge transfer by reducing the free water vapour concentration in chamber 22. Consequently, a greater number of molecular ions reach detector 32 significantly improving the sensitivity of the mobility spectrometer. Alternatively, in some applications heating or cooling may be employed to reduce the water vapour concentration in gas 34. However, in other applications where the maximum degree of sensitivity is not required the carrier gas may be omitted.

Figure 2:
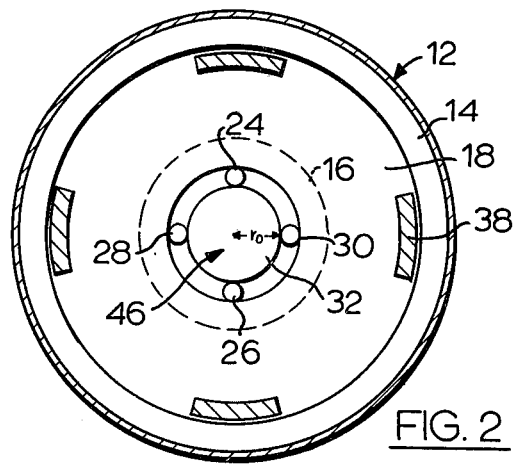
FIG. 2 is a vertical sectional view taken on lines 2—2 of FIG. 1.
Figure 3:
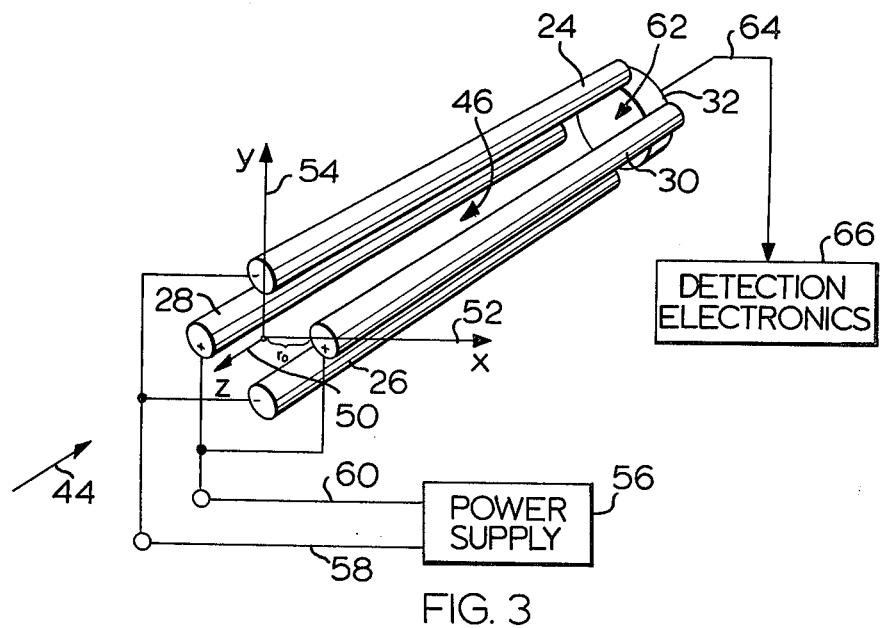
FIG. 3 is a diagrammatic view of the electrical circuitry necessary to the operation of the present invention.

Reference is next made to FIG. 2. The carrier gas molecular ion mixture is carried into chamber 22 by the axial flow of gas 34. The mixture is directed into an inner electrode region 46 by means of an orifice formed at the entry side of chamber 22 by an inwardly projecting flange 48. The electric field in the inner electrode region is created by applying a predetermined voltage waveform generated by a bipolar power supply 56 to electrode pairs 24, 26 and 28, 30.

The power supply 56 is connected to electrode pairs 24, 26 and 28, 30 by leads 58 and 60 respectively. The transverse hyperbolic electric field thus created is periodic in time, symmetrical with respect to the z-axis 50 and depends quadratically on the distance from the x-axis 52 and the y-axis 54. Consequently the electric field produced at or near the z-axis can in approximation be expressed mathematically as:

$$\Phi(x,y,z,t) = F(t) \cdot \frac{x^2 - y^2}{r_o^2} \qquad (1)$$

where $\Phi(x, y, z, t)$ is an electric field potential function in volts $f(t)$ is a voltage waveform having an arbitrary periodic form with time in volts $x$ is the distance along the x-axis in cms.

$y$ is the distance along the y-axis in cms.

$r_o$ is one-half the diametrical distance between electrodes in cms. (see FIGS. 2 and 3).

The basic equation of motion of a molecular ion present in an electric field of the general form $\Phi(x, y, z, t)$ can be expressed as:

$$v = K.E$$
$$= -K. \Delta \Phi(x, y, z, t) \qquad (2)$$

In the preferred embodiment of the present invention a voltage waveform $f(t)$ is generated by power supply 56 and is a sinusoidal voltage superimposed on a ramp voltage and can be expressed as:

$$f(t) = U'.t + U_m \sin\omega_m t \qquad (3)$$

where $U'$ is a constant in volts/second $t$ is time in seconds $U_m$ is the peak amplitude of the sinusoidal voltage in volts $\omega_m$ is the frequency of the sinusoidal voltage in radians/second The generalized equations of motion along each coordinate axis can thus be expressed by the following differential equations:

$$\frac{d^2x}{dt^2} + \frac{2 \cdot k}{r_o^2}[U' + \omega_m \cdot U_m \cdot \cos \omega_m t] \cdot x = 0 \qquad (4)$$

$$\frac{d^2y}{dt^2} - \frac{2 \cdot k}{r_o^2}[U' + \omega_m \cdot U_m \cdot \cos \omega t] \cdot y = 0 \qquad (5)$$

$$\frac{d^2z}{dt^2} = 0 \qquad (6)$$

The solution of differential equations (4), (5) and (6) yields a trajectory stability requirement dependent on molecular ion mobility. Therefore, in order for any molecular ion species to have a stable trajectory through inter-electrode region 46 the molecular ion species may characterized by the following mathematical relationship:

$$\frac{1}{K} = \frac{5.7 \cdot U_m}{\omega_m \cdot r_o^2} \qquad (7)$$

Another important parameter of a mobility spectrometer is its resolution. The resolution of mobility spectrometer relates to its ability to restrict the passage of molecular ions through the inner electrode space to a particular value or range of values of molecular ion mobility. In this respect a mobility spectrometer can be analogized to a mass filter which can in effect be tuned to allow only those molecular ions having a predetermined mass to pass through. In a mobility spectrometer stable molecular ion trajectories will ordinarily exist only for either a single value or a relatively small range of values of molecular ion species masses depending on the manner in which the mobility spectrometer is used. Only those molecular ions whose mobility corresponds to the required mobility or range of values of mobility will pass through inner electrode space 46 and strike detector 32. The resolution depends mathematically on:

$$R_m = \frac{U'}{\omega_m \cdot U_m} \qquad (8)$$

Where $R_m$ is a dimension less parameter which defines the resolution of a mobility spectrometer and $U'$, $U_m$ and $\omega_m$ have been previously defined.

It is apparent from equation (8) that $R_m$ may be made electronically variable by altering $U'$, $U_m$ or $\omega_m$. Resolution is a function of $R_m$. A theoretical estimate is $$\left|\frac{K}{\Delta K}\right| = \frac{m}{\Delta m} = \frac{0.75}{1 - R_m/(R_m) \text{ max}} \text{ where } (R_m) \text{ max} = 0.167$$

Thus in theory, resolution is infinite when $R_m \rightarrow (R_m)$ max. Thus, if $U'$, $U_m$ and $\omega_m$ are selected so that $R_m = 0.167$ a stable molecular ion trajectory will exist for only one particular value of molecular ion mass. Only molecular ions having this particular mass will pass through the inner electrode space to strike detector 32. If $R_m$ is greater than 0.167 no stable trajectories will exist for any value of mass and consequently no molecular ions will emerge from the inner electrode space to strike detector 32. On the other hand if $R_m$ is less than 0.167 more than one value of molecular ion mass will have a stable trajectory and will emerge to strike detector 32. Consequently, by varying $R_m$ the mass resolution of a mobility spectrometer can be varied as desired.

It has been observed that the value of molecular ion mobility $k$ generally decreases monotonically with a power law slightly less than unity with respect to molecular ion size and that the molecular ion size bears an almost direct relationship to molecular ion mass. Thus not only by analogy is $$\frac{k}{\Delta k} = \frac{m}{\Delta m},$$

but if $$K \alpha \frac{1}{m}$$

then it is mathematically so. Consequently, a repetitive amplitude scan of $U_m$ in time, at constant $\omega_m$, while maintaining a fixed value for $R_m$, will yield a quasi-linear mass scan at constant resolution throughout the range of molecular ion masses being examined. The ability to perform a mass scan at a constant value of mass resolution represents a very important feature of the mobility spectrometer.

For selected values of $r_o$, $U_m$ and $\omega_m$ and a fixed value for $R_m$ of less than or equal to 0.167 molecular ions will emerge from the inner electrode space 46 into region 62 (see FIGS. 1 & 3) having a specific molecular ion mobility and hence a specific mass. All other molecular ions will have executed unstable trajectories while in the inner electrode region 46 and hence will be discharged by colliding with one or other of the four electrodes, 24, 26, 28 and 30. The emerging molecular ions eventually will collide with detector 32, preferably an electrometer or similar type detector, where they are collected and directed by a lead 64 to detection electronics 66. The detection electronics serves to amplify, process and display the signal, created when the emerging molecular ions strike detector 22. The display is in effect a signature of the molecular specie, present in gas 34.

The theory and apparatus according to the present invention as described may now be applied to a practical apparatus in order to determine the required parameters of electrodes 24, 26, 28 and 30 and power supply 56. The voltage $f(t)$ as defined by equation (3) represents a ramp waveform with a slope $U'$ upon which is superimposed a sinusoidal waveform of frequency $\omega_m$ and amplitude $U_m$. In a practical mobility spectrometer the ramp waveform $U't$ must be bounded particularly if repetitive mass scanning is employed. As a result a ramp waveform having a finite amplitude $U$ and a slope $U'$ may be employed. If the fall time of the ramp waveform is very rapid the displacement of the molecular ions in inner electrode region 46 during the fall time will be negligible and can be ignored. Consequently, a ramp voltage having a sinusoidal oscillation superimposed upon it can be used to closely approximate the theoretically derived form of $f(t)$.

If the frequency of the sawtooth waveform is $\omega_1$ then $$U' = \frac{U \cdot \omega_1}{2\pi}.$$

A mobility scan is achieved by varying $U_m$ as described above from a predetermined lower value to a predetermined maximum value while maintaining $R_m$ constant.

$$\text{Since } R_m = \frac{U'}{\omega_m \cdot U_m} = \frac{U \cdot \omega_1}{2\pi \cdot \omega \cdot U_m}$$

the mass resolution can be held constant by varying $U$ as well as $U_m$ while at the same time keeping the ratio of their values constant.

In order to achieve adequate molecular ion species separation the molecular ions which pass through the mobility spectrometer to detector 32 should undergo typically 100 oscillations while in inner electrode space 46. Considering the limitation of 600 inches per second imposed on the axial speed of gas 34 to ensure laminar flow in outer housing 12 this implies electrode lengths measured in inches. This in turn results in the fundamental operating frequency $\omega_m$ being $\gtrsim 7 \times 10^4$ radians per second.

In the preferred embodiment of the present invention $r_o = 0.2$ cm. In order to obtain a satisfactory approximation to the hyperbolic electric field in inner electrode region 46 as defined by equation (2) while employing cylindrical electrodes an electrode/diameter of approximately 0.5 cm. is required. Considering that the apparatus as defined by the present invention will be employed to measure a maximum molecular ion mass of approximately 1,000 atomic mass units, $k$ may be typically at 0.5 cms.$^2$/ volt-second. Equation (7) can be used to compute the maximum value of $U_m$ assuming a typical value for $\omega_m$ of $3 \times 10^4$ radians per second. As a result, the maximum value required for $U_m$ during a mass scan covering a mass range of up to 1000 atomic mass units is approximately 400 volts. The maximum value of the ramp amplitude $U$ can be computed from the equation:

$$\frac{U \cdot \omega_1}{2 \pi \cdot \omega_m \cdot U_m} = 0.167$$

For simplicity the ramp frequency $\omega_1$ may be set equal to $\omega_m$. However, it should be emphasized that $\omega_1$ may take on other values and furthermore, whether or not $\omega_1$ is set equal to $\omega_m$ no phase relationship between the two frequencies is required. The result is that $U$ has a peak value of approximately 400 volts and $U'$ therefore is approximately equal to $2 \times 10^6$ volts per second.

Having specified the peak amplitude levels and frequencies of the ramp and sinusoidal voltages forming $f(t)$ power supply 56 has been essentially defined. Because the mobility spectrometer requires relatively low voltages and frequencies power supply 56 may be a commercially available programmable DC power supply. The sawtooth voltage fall time being at least 10 times faster than the ramp slope $U'$ does not present a problem since the power requirement of the mobility spectrometer is virtually nil involving only the charging and discharging of electrodes 24, 26, 28 and 30.

The response time of the mobility spectrometer may be defined as the time required to reliably detect the particular species of molecular ion passing through the apparatus. The response generally depends on the time constant of detector 32 and the concentration of molecular ion species involved. Considering a beta source of $10^{-7}$ amperes and typically expected ion concentrations and employing an electrometer for detector 32 a typical response time would be in the range of 0.1 to 25 seconds.

It will be appreciated by those skilled in the art that the mobility spectrometer described and illustrated in the foregoing description and drawings represents a preferred embodiment of the present invention. Modifications and changes may be made therein without the departing from the spirit of the present invention. Specifically, the electrode dimensions and spacings may be altered to suit different classes of molecular ion species and the voltage waveform $f(t)$ may be similarly altered in terms of the peak voltages employed and the frequencies used. Furthermore, both positive and negative ions can be analyzed by employing a bipolar form of detector 32.

What I claim is:

1. A method of analyzing predetermined molecular species present in a gas based on differences in molecular ion mobility of said molecular species comprising: ionizing said molecular species to form stable charged molecular ions, producing a flow of a carrier gas, causing said ions and carrier gas to flow in a stream, producing a transverse hyperbolic electric field in a region having a longitudinal axis, said field varying in time and quadratically with distance from said longitudinal axis and said field being defined by the sum of a sawtooth waveform having a predetermined amplitude and frequency and a sinusoidal waveform having a predetermined amplitude and frequency, directing said molecular ions through said region symmetrically about said longitudinal axis and detecting molecular ions which have passed through said region, whereby upon entry into said region the molecular ions undergo oscillatory trajectories, said trajectories being stable only for molecular ions of predetermined mobility and predetermined amplitudes and frequencies of said sawtooth and sinusoidal waveforms.

2. A method as claimed in claim 1 wherein said region is defined by four parallel electrodes of predetermined length each spaced a distance $r_0$ from said longitudinal axis, and wherein the motion of said stable ions through said region is defined by the formula $$\frac{1}{K} = \frac{5.7 \cdot U_m}{\omega_m \cdot r_0^2}$$

where $K$ = molecular ion mobility $U_m$ = peak amplitude of the sinusoidal function, and $\omega_m$ = frequency of the sinusoidal function 3. An apparatus for analyzing predetermined molecular species present in a gas based on the differences in molecular ion mobility of said molecular species comprising;

a. means for ionizing said molecular species to form ions,
b. means for producing a flow of a carrier gas,
c. means for causing the carrier gas and the ions to flow in a stream,
d. means for producing a transverse hyperbolic electric field in a region having a longitudinal axis,
e. means for directing said ions through said region,
f. said electric field being defined by the sum of a voltage having a sawtooth waveform of predetermined amplitude and frequency and a voltage having a sinusoidal waveform of predetermined amplitude and frequency,
g. means for detecting molecular ions after they have passed through said region,
h. whereby upon entry into said region said molecular ions undergo oscillatory trajectories, said trajectories being stable for molecular ions of predetermined mobility and for predetermined amplitudes and frequencies of said sawtooth and sinusoidal waveforms.

4. Apparatus as claimed in claim 3 wherein said electric field producing means comprises four mutually parallel generally cylindrical electrodes of predetermined length and diameter each based from said longitudinal axis by a distance $r_0$, wherein opposite ones of said electrodes are electrically interconnected to form two opposing pairs of electrodes, and a bipolar power supply electrically connected to said opposing pairs of electrodes for energizing said electrodes with a voltage having a waveform characterized by a sawtooth voltage of predetermined peak amplitude and frequency upon which is superimposed a sinusoidal voltage of predetermined amplitude and frequency, the motion of said stable ions in the region between said electrodes being defined by the formula:

$$\frac{1}{K} = \frac{5.7 \, U_m}{\omega_m \cdot r_0^2}$$

where $K$ = molecular ion mobility $U_m$ = peak amplitude of the sinusoidal function, and $\omega_m$ = frequency of the sinusoidal function 5. Apparatus as claimed in claim 4 including means for adjusting the amplitude of said sinusoidal voltage to permit ions of different predetermined mobility to pass through said region.

6. Apparatus as claimed in claim 4 including means for adjusting the amplitudes of said sinusoidal and sawtooth voltages periodically between predetermined upper and lower limits while keeping the ratio of said voltages constant.

* * * * *